(12) United States Patent
Yamada et al.

(10) Patent No.: US 9,201,040 B2
(45) Date of Patent: Dec. 1, 2015

(54) GAS SENSOR

(75) Inventors: Yuichi Yamada, Komaki (JP); Takahiro Akiyama, Komaki (JP); Takuya Saito, Kasugai (JP); Makoto Kume, Inuyama (JP); Satoshi Teramoto, Nisshin (JP); Noboru Matsui, Iwakura (JP); Hiroshi Inagaki, Komaki (JP); Takeshi Kawai, Komaki (JP); Shinichiro Iwama, Komaki (JP)

(73) Assignee: NGK SPARK PLUG CO., LTD., Nagoya-shi (JP)

( * ) Notice: Subject to any disclaimer, the term of this patent is extended or adjusted under 35 U.S.C. 154(b) by 713 days.

(21) Appl. No.: 13/176,106

(22) Filed: Jul. 5, 2011

(65) Prior Publication Data

US 2012/0006093 A1   Jan. 12, 2012

(30) Foreign Application Priority Data

Jul. 6, 2010   (JP) .................................. 2010-154335

(51) Int. Cl.
  *G01M 15/10* (2006.01)
  *G01N 27/407* (2006.01)
(52) U.S. Cl.
  CPC .................................. *G01N 27/4078* (2013.01)
(58) Field of Classification Search
  USPC ........... 73/23.31, 23.32, 31.05; 204/424, 425, 204/426, 427, 428, 429, 431, 432
  See application file for complete search history.

(56) References Cited

U.S. PATENT DOCUMENTS

| | | | | |
|---|---|---|---|---|
| 3,691,512 A | * | 9/1972 | Exner | 439/660 |
| 4,352,714 A | * | 10/1982 | Patterson et al. | 216/33 |
| 4,377,801 A | * | 3/1983 | Weber et al. | 338/34 |
| 4,489,596 A | * | 12/1984 | Linder et al. | 73/114.19 |
| 4,720,993 A | * | 1/1988 | Badwal | 73/31.05 |
| 4,823,803 A | * | 4/1989 | Nakamura | 600/530 |
| 5,172,466 A | * | 12/1992 | Friese et al. | 29/612 |
| 5,181,007 A | * | 1/1993 | Friese et al. | 338/22 R |
| 5,247,158 A | * | 9/1993 | Steinhauser et al. | 219/544 |
| 5,329,806 A | * | 7/1994 | McClanahan et al. | 73/31.05 |
| 5,455,209 A | * | 10/1995 | Powell | 501/17 |
| 5,569,475 A | * | 10/1996 | Adas et al. | 425/549 |
| 5,593,558 A | * | 1/1997 | Sugino et al. | 204/429 |
| 5,689,059 A | * | 11/1997 | Oh et al. | 73/23.31 |
| 5,929,327 A | * | 7/1999 | Hafele | 73/114.75 |
| 5,935,460 A | * | 8/1999 | Mori et al. | 219/121.59 |
| 5,996,337 A | * | 12/1999 | Blosser et al. | 60/274 |

(Continued)

FOREIGN PATENT DOCUMENTS

| | | | | |
|---|---|---|---|---|
| GB | 2003272 A | * | 3/1979 | ............. G01N 27/04 |
| JP | 2009-216388 A | | 9/2009 | |

*Primary Examiner* — Hezron E. Williams
*Assistant Examiner* — Mark A Shabman
(74) *Attorney, Agent, or Firm* — Sughrue Mion, PLLC

(57) ABSTRACT

A gas sensor including coating layers (64) and (69) of fluorine or a fluorine compound formed on the surface of a separator (60), including a front separator (61) and a rear separator (66), disposed inside a sheath (30). The coating layers (64) and (69) have water impermeability and water repellency. Even in the case where moisture contained in the atmosphere within a sheath (30) forms dew on the surface of the separator (60), the coating layers (64) and (69) prevent soaking of moisture into the separator (60), to thereby secure the insulation property of the separator (60). Also, the coating layers (64) and (69) having water repellency prevent a water droplet from spreading on the surface of the separator (60) with resultant formation of a film of water, to thereby prevent flow of leakage current via a film of water.

5 Claims, 2 Drawing Sheets

(56) References Cited

U.S. PATENT DOCUMENTS

| | | | |
|---|---|---|---|
| 6,155,212 A * | 12/2000 | McAlister | 123/3 |
| 6,165,336 A * | 12/2000 | Maki et al. | 204/415 |
| 6,360,581 B1 * | 3/2002 | Murase et al. | 73/23.2 |
| 6,484,561 B2 * | 11/2002 | Jackson et al. | 73/31.05 |
| 6,512,204 B1 * | 1/2003 | Chiu et al. | 219/270 |
| 7,073,388 B2 * | 7/2006 | Mei | 73/718 |
| 7,081,274 B2 * | 7/2006 | Nishikawa et al. | 427/376.2 |
| 7,338,202 B1 * | 3/2008 | Kapat et al. | 374/10 |
| 7,677,097 B2 * | 3/2010 | Tokuyasu et al. | 73/204.15 |
| 7,708,869 B2 * | 5/2010 | Yamada | 204/428 |
| 2001/0054552 A1 * | 12/2001 | Matsuo et al. | 204/421 |
| 2004/0149032 A1 * | 8/2004 | Sell | 73/304 C |
| 2005/0092729 A1 * | 5/2005 | Konishi et al. | 219/229 |
| 2008/0067066 A1 * | 3/2008 | Okumura et al. | 204/424 |
| 2008/0223110 A1 * | 9/2008 | Weyl et al. | 73/31.05 |
| 2008/0257016 A1 * | 10/2008 | Fujii et al. | 73/31.05 |
| 2009/0071231 A1 * | 3/2009 | Fujii et al. | 73/31.05 |
| 2009/0100907 A1 * | 4/2009 | Mizutani et al. | 73/31.05 |
| 2009/0223818 A1 | 9/2009 | Matsui et al. | |

\* cited by examiner

GAS SENSOR

TECHNICAL FIELD

The present invention relates to a gas sensor which includes a detection element for detecting the concentration of a specific gas.

BACKGROUND ART

There has been known a gas sensor which is attached to an exhaust passage of an internal combustion engine, such as an automotive engine, and which includes a detection element whose output changes in accordance with the concentration of a specific gas (for example, $NO_x$ (nitrogen oxides) or oxygen) within exhaust gas. The detection element includes at least one cell composed of a solid electrolyte member and a pair of electrodes provided thereon, and the output of the detection element (current flowing through the cell or electromotive force generated by the cell) changes in accordance with the concentration of the specific gas. This detection element has, at its front end, a detection portion whose output changes in accordance with the concentration of the specific gas. The circumference of a trunk portion of the detection element is surrounded by a metallic shell which is adapted to attach the gas sensor to an exhaust pipe, and the detection element is gas-tightly held by a sealing filler, such as talc, boron nitride, or glass, provided within the metallic shell. A rear end portion of the detection element projects rearward from the metallic shell, and is surrounded by a sheath attached to a rear end portion of the metallic shell. An elastic member formed of rubber is fitted into a rear end portion of the sheath, whereby the interior of the sheath is sealed.

In order to take out the output from the detection portion located at the front end, a plurality of output take-out portions are provided on the rear end portion of the detection element (for example, electrode pads are formed on the surface of the rear end portion of the detection element). A plurality of lead wires for electrically connecting the detection element and an external circuit are passed through the elastic member, and conduction members (metallic terminals) provided at the ends of the lead wires are connected to the output take-out portions (electrode pads). Moreover, a separator formed of an electrically insulating ceramic is disposed inside the sheath. The conduction members are accommodated in the separator such that they do not have contact with one another (for example, see Patent Document 1). Also, this separator secures insulation between the conduction members and the sheath.

PRIOR ART DOCUMENT

Patent Document

[Patent Document 1] Japanese Patent Application Laid-open (kokai) No. 2009-216388

SUMMARY OF THE INVENTION

Problems to be Solved by the Invention

However, in the case where the atmosphere within the sealed sheath contains moisture, the following problem arises. When dew formation occurs within the sheath due to a change in temperature or humidity of the surrounding atmosphere, a water droplet adheres to the surface of the separator, and moisture may soak into the separator. If the insulation resistance of the separator itself drops due to the soaking with moisture, it becomes difficult to secure insulation (high insulation resistance) between the conduction members electrically connected to the detection element, whereby a proper output cannot be obtained from the detection element. Examples of the case where the atmosphere within the sheath contains humidity include a case where moisture absorbed by a sealing filler within the metallic shell is released.

The present invention has been conceived in view of the above problem, and an object of the invention is to provide a gas sensor in which the insulation among conduction members is stably secured through stable maintenance of the insulation property of a separator provided within a sheath, whereby a normal output can be obtained from a detection element.

Means for Solving the Problems

According to one mode of the present invention, there is provided a gas sensor comprising a detection element extending in an axial direction and adapted to detect the concentration of a specific gas; a metallic shell circumferentially surrounding and holding the detection element; a sheath attached to a rear end portion of the metallic shell and surrounding a rear end portion of the detection element; and a separator formed of an electrically insulating ceramic, disposed inside the sheath, and accommodating at least a plurality of conduction members for electrical connection with the detection element, the gas sensor being characterized in that a coating layer having water impermeability is formed on at least a surface of the separator.

Since the coating layer formed on the surface of the separator formed of an electrically insulating ceramic has water impermeability, even when dew formation occurs inside the sheath due to a change in the temperature or humidity of the surrounding environment, soaking of water into the separator can be prevented. Therefore, it is possible to prevent a water droplet adhering to the surface of the separator from decreasing the insulation resistance of the separator, to thereby prevent deterioration of insulation among the conduction members accommodated inside the separator.

In the present mode, the coating layer may have water repellency. In the case where the coating layer has water repellency, even when a water droplet adheres to the surface of the separator, the droplet does not spread, which would otherwise occur due to surface tension, whereby formation of a film of water can be prevented. Thus, there is no possibility that leakage current flows (e.g., between the conduction members and the sheath) via a water film formed on the surface of the separator.

In the present mode, the coating layer may be formed of glass. When a coating layer of glass is formed, water impermeability and heat resistance are attained. Since the gas sensor may be influenced by the heat of hot gas, formation of a coating layer having heat resistance is desirable from the viewpoint of maintaining the insulation performance of the separator over a long period of time. Also, the durability of the coating layer can be secured.

In the present mode, the detection element may include electrode pads formed on a rear end portion thereof for electrical connection with the conduction members. The separator may accommodate the rear end portion of the detection element. The electrical connection between the conduction members and the electrode pads may be established inside the separator. When a water droplet adheres to the surface of the separator, leakage current flows between the conduction members (the detection element) and the sheath in many cases. Since areas (contact points) in which the conduction members and the electrode pads are electrically connected together are accommodated within the separator, the contact points can be prevented from being exposed, and leakage current between the contact points and the sheath can be prevented.

MODE FOR CARRYING OUT THE INVENTION

Figure 1:
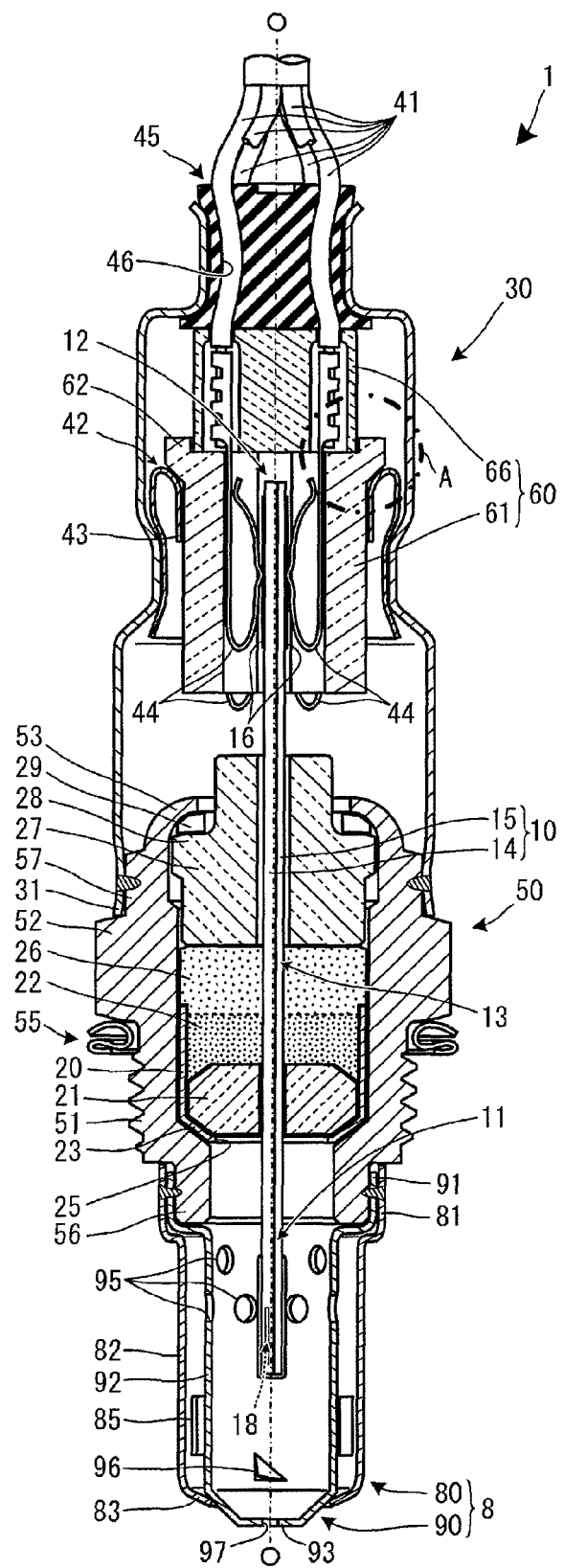
[FIG. 1] Sectional view of an $NO_x$ sensor 1.

A gas sensor according to an embodiment of the present invention will next be described with reference to the drawings. First, the structure of an $NO_x$ sensor 1 will be described, by way of example, with reference to FIG. 1. In FIG. 1, the direction of an axis O (represented by a dash-dot line) of the $NO_x$ sensor 1 coincides with the vertical direction. In the following description, a side toward a front end portion 11 of a detection element 10 held in the $NO_x$ sensor 1 is referred to as a front end side of the $NO_x$ sensor 1, and a side toward a rear end portion 12 thereof is referred to as a rear end side of the $NO_x$ sensor 1.

The $NO_x$ sensor 1 shown in FIG. 1 is attached to an exhaust pipe (not shown) of an automobile. A detection portion 18 of the detection element 10 held in the $NO_x$ sensor 1 is exposed to exhaust gas which flows through the exhaust pipe, for detecting the concentration of $NO_x$ (specific gas) contained in the exhaust gas.

As is well known, the detection element 10 assumes the form of a plate of narrow width extending in the direction of the axis O. The detection element 10 is a substantially rectangular columnar laminate in which a gas detection body 14 for detecting the concentration of $NO_x$, and a heater 15 for promptly activating the gas detection body 14 through application of heat are stacked on each other. Notably, in FIG. 1, the plate thickness direction corresponds to the left-right direction of the sheet, and the plate width direction corresponds to the front-back direction of the sheet (direction perpendicular to the sheet). The gas detection body 14 includes, for example, a first oxygen pump cell and a second oxygen pump cell each composed of a solid electrolyte member mainly formed of zirconia, and a pair of electrodes formed thereon. Since the structure of the gas detection body 14 is disclosed by Japanese Patent Application Laid-open (kokai) No. 2010-122187, its detailed description is omitted. The detection portion 18 including the above-described second oxygen pump cell, etc. (in other words, a portion for detecting the concentration of $NO_x$) is located at the front end of the detection element 10 (the gas detection body 14). Also, six electrode pads 16 (FIG. 1 shows two of them) are formed on a rear end portion 12 of the detection element 10 for electrical connection with the gas detection body 14 and the heater 15. Notably, in the present embodiment, the detection element 10 is described as the "detection element" of the present invention. However, strictly speaking, the heater 15 is not necessarily required to be a constituent of the detection element, and the gas detection body 14 corresponds to the "detection element" of the present invention.

A closed-bottomed tubular metal cup 20 is disposed slightly frontward of the axial center of a trunk portion 13 of the detection element 10, and has an opening 25 formed in the bottom wall thereof. The detection element 10 is inserted through the interior of the metal cup 20 such that its front end portion 11 at which the detection portion 18 is formed projects frontward from the opening 25. The metal cup 20 is a member for holding the detection element 10 in a metallic shell 50. A front-end peripheral-portion 23 located at a peripheral portion of the bottom wall of the metal cup 20 is tapered toward a circumferential wall portion of the metal cup 20. A ceramic ring 21 made of alumina and a talc ring 22 formed by compacting a talc powder are disposed within the metal cup 20 such that they are laminated in the direction of the axis O, and surround the circumference of the detection element 10. The talc ring 22 is crushed within the metal cup 20 so as to tightly fill an associated space, thereby holding the detection element 10 in position in the metal cup 20.

An assembly of the metal cup 20 and the detection element 10 is surrounded by and held by the tubular metallic shell 50. The metallic shell 50 is adapted to fixedly attach the $NO_x$ sensor 1 to the exhaust pipe (not show) of an automobile. The metallic shell 50 has a mounting portion 51 which is formed on an outer circumferential surface of the metallic shell 50 and located on a side toward the front end of the metallic shell 50. The mounting portion 51 has an external thread formed thereon for attachment to the exhaust pipe. The metallic shell 50 has a front-end engagement portion 56 which is located frontward of the mounting portion 51 and with which a protector 8 to be described later is engaged. The metallic shell 50 also has a tool engagement portion 52 which is formed at an axially central portion of the outer circumferential surface of the metallic shell 50 and with which a mounting tool is engaged. The metallic shell 50 further has a rear-end engagement portion 57 which is located rearward of the tool engagement portion 52 and with which a sheath 30 to be described later is engaged, and a crimp portion 53 which is located rearward of the rear-end engagement portion 57 and adapted to crimp-hold the detection element 10 in the metallic shell 50. In order to prevent leakage of gas when the $NO_x$ sensor 1 is attached to the exhaust pipe, an annular gasket 55 is fitted to a portion of the metallic shell 50 between the tool engagement portion 52 and the mounting portion 51.

The metallic shell 50 has a stepped portion on its inner circumferential surface at a position near the mounting portion 51. The front-end peripheral-portion 23 of the metal cup 20, which holds the above-described detection element 10, is engaged with the stepped portion. Furthermore, a talc ring 26 is placed into the metallic shell 50 along the inner circumference of the metallic shell 50 toward the rear end of the metal cup 20 in such a state that the detection element 10 is inserted through the talc ring 26. A tubular sleeve 27 is fitted into the metallic shell 50 such that the sleeve 27 presses the talc ring 26 from the rear end side of the talc ring 26 and the detection element 10 extends through the sleeve 27. The sleeve 27 has a step-like shoulder portion 28 formed on the outer circumferential surface of a rear end portion of the sleeve 27. An annular packing 29 is disposed on the shoulder portion 28. In this condition, the crimp portion 53 of the metallic shell 50 is crimped radially inward in such a manner as to press the shoulder portion 28 of the sleeve 27 frontward via the packing 29. As a result of this crimping, the talc ring 26, which is pressed by the sleeve 27, is crushed within the metallic shell 50, thereby tightly filling an associated space. By means of the talc ring 26 and the talc ring 22, which is previously placed in the metal cup 20, the metal cup 20 and the detection element 10 are held in position in the metallic shell 50.

The front-end engagement portion 56 of the metallic shell 50 is formed into a tubular shape, and the protector 8 is fitted thereon. The protector 8 surrounds the circumference of the front end portion 11 of the detection element 10 to thereby protect the detection element 10 from water, breakage caused by physical impact, etc. The protector 8 is fixed to the front-end engagement portion 56 by means of resistance welding or laser welding. The protector 8 has a double structure; i.e., is composed of a bottomed tubular inner protector 90 and a tubular outer protector 80 which circumferentially surrounds the inner protector 90 while forming a clearance between the inner circumferential surface of the outer protector 80 and the outer circumferential surface of the inner protector 90.

The inner protector 90 has a plurality of inner introduction holes 95 formed in a rear end portion of a circumferential wall 92 thereof, a plurality of drain holes 96 formed in a front end portion of the circumferential wall 92, and a discharge opening 97 formed in a bottom wall 93 thereof. A base end portion 91 of the inner protector 90 located on the side toward the open end thereof (the rear end side) is engaged with the outer circumference of the front-end engagement portion 56. The outer protector 80 includes a plurality of outer introduction holes 85 formed in a front end portion of a circumferential wall 82 thereof. A base end portion 81 of the outer protector 80 located on the side toward the open end thereof is engaged with the outer circumference of the base end portion 91 of the inner protector 90. In this state, laser welling is performed on the outer circumference of the base end portion 81, whereby the base end portion 81 is joined to the front-end engagement portion 56 of the metallic shell 50, along with the base end portion 91 of the inner protector 90. Thus, the outer protector 80 and the inner protector 90 are fixed to the metallic shell 50. Moreover, a front end portion 83 of the outer protector 80 is bent inward toward the circumferential wall 92 of the inner protector 90 so as to close the clearance between the outer protector 80 and the inner protector 90.

Meanwhile, the rear end portion 12 of the detection element 10 held by the metallic shell 50 projects rearward beyond the rear end (crimp portion 53) of the metallic shell 50. The rear end portion 12 is covered with a tubular separator 60 formed from an electrically insulating ceramic (in the present embodiment, alumina). The separator 60 is composed of a front separator 61 and a rear separator 66. The rear separator 66 is in engagement with a flange portion 62 of the front separator 61, which portion projects radially outward from the front separator 61. The front separator 61 accommodates connection portions (connection points) between the six electrode pads 16 formed on the rear end portion 12 of the detection element 10 and the six connection terminals (metallic terminals) 44 (FIG. 1 shows four of them) electrically connected to the corresponding electrode pads 16. In other words, electrical connection between the connection terminals 44 and the electrode pads 16 is established inside the front separator 61. The rear separator 66 accommodates connection portions between the connection terminals 44 and six lead wires 41 extending to the outside of the $NO_x$ sensor 1.

The tubular metal sheath 30 is disposed in such a manner as to surround the rear end portion 12 of the detection element 10 to which the separator 60 is fitted. A front open end 31 of the sheath 30 is engaged with the outer circumference of the rear-end engagement portion 57 of the metallic shell 50. The open end 31 is crimped radially inward, and laser welding is performed on the open end 31 along the entire outer circumference of the open end 31, whereby the open end 31 is joined to the rear-end engagement portion 57. The sheath 30 and the metallic shell 50 are thus fixedly united together.

A tubular metal holder 42 is disposed in the gap between the sheath 30 and the front separator 61. The metal holder 42 has a support portion 43, which is formed by inwardly bending a rear end of the metal holder 42. The front separator 61 is inserted through the metal holder 42 such that the flange portion 62 of the front separator 61 is engaged with the support portion 43, whereby the front separator 61 is supported by the metal holder 42. In this condition, a portion of the sheath 30 where the metal holder 42 is disposed is crimped radially inward, whereby the metal holder 42, which supports the front separator 61, is fixed to the sheath 30.

Next, an elastic member 45 of fluorine-containing rubber is fitted into a rear end opening of the sheath 30, whereby the interior of the sheath 30 is sealed. The elastic member 45 has six insertion holes 46 (FIG. 1 shows two of them). The above-mentioned six lead wires 41 extending from the separator 60 extend through the respective insertion holes 46. In this condition, while the elastic member 45 presses the rear separator 66 against the front separator 61, the sheath 30 is crimped radially inward, whereby the elastic member 45 is fixed to the rear end of the sheath 30.

Figure 2:
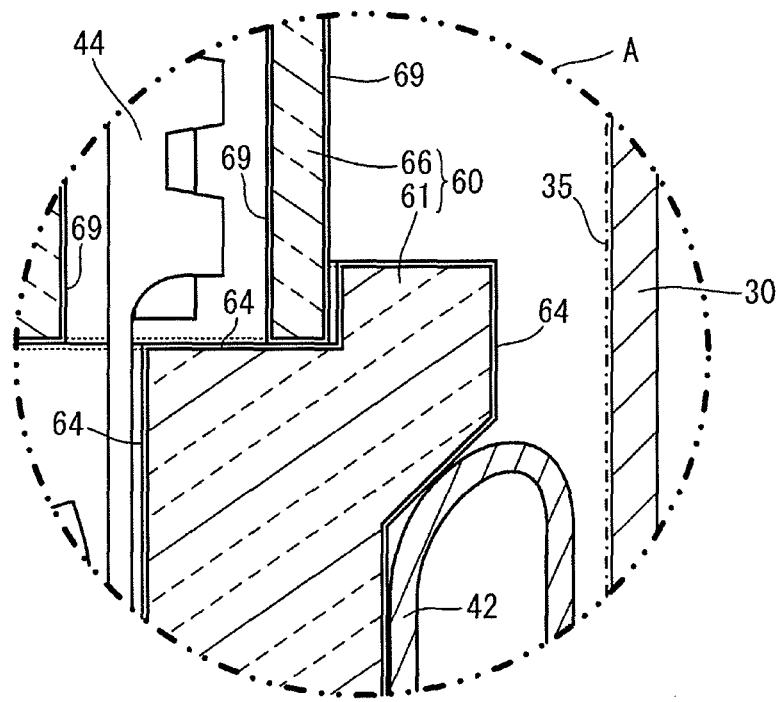
[FIG. 2] Enlarged view of a portion of FIG. 1 surrounded by a dash-dot-dot line A.

In the case of the $NO_x$ sensor 1 of the present embodiment, coating is applied to the surface of the separator 60. Specifically, as shown in FIG. 2, a coating layer 64 is formed on the entire surface of the front separator 61, which partially constitutes the separator 60, and a coating layer 69 is formed on the entire surface of the rear separator 66, which partially constitutes the separator 60. For example, the coating layers 64 and 69 of the present embodiment are formed of fluorine or a fluorine compound (e.g., Teflon (registered trademark)), and have water impermeability (waterproofness) and water repellency.

As described above, the front separator 61 and the rear separator 66 are disposed inside the sheath 30. In the case where the atmosphere within the sheath 30 contains moisture, dew formation occurs on the surfaces of the front separator 61 and the rear separator 66, and a water droplet may adhere to the surfaces. Even in such a case, since the coating layers 64 and 69 formed on the surface of the separator 60 have water impermeability, moisture does not soak into the front separator 61 and the rear separator 66. Accordingly, there is no possibility that moisture having soaked into the separator 60 decreases the insulation resistance of the separator 60, whereby the insulation among the connection terminals 44 cannot be secured. Furthermore, since the coating layers 64 and 69 have water repellency, a water droplet adhering to the surface of the separator 60 does not spread, which spread would otherwise occur because of surface tension thereof with resultant formation of a film of water. Accordingly, there is no possibility that leakage current flows between the connection terminals 44 and the sheath 30 via the metal holder 42, which flow of leakage current would otherwise occur via a film of water formed on the surface of the separator 60. As described above, in the present embodiment, since the coating layers 64 and 69 are provided on the surface of the separator 60, the insulation property of the separator 60 can be maintained for a long period of time, whereby an $NO_x$ sensor 1 having high reliability can be provided.

Also, in the present embodiment, through employment of a structure in which the separator 60 covers the rear end portion 12 of the detection element 10, the connection portions (contact points) between the connection terminals 44 and the electrode pads 16 are accommodated inside the separator 60. Thus, the contact points can be protected from exposure. Therefore, even when a film of water is formed on the surface of the separator 60, leakage current between the contact points and the sheath 30 can be prevented.

Notably, the present invention is not limited to the above-described embodiment, and various modifications are possible. In the present embodiment, the coating layers 64 and 69 on the surface of the separator 60 are formed of fluorine or a fluorine compound. However, the material of these coating layers is not limited thereto, and the coating layers 64 and 69 may be formed of glass. When the coating layers 64 and 69 of glass are formed, water impermeability and heat resistance can be attained. Since the $NO_x$ sensor 1 is attached to an exhaust pipe for use and may be influenced by the heat of hot exhaust gas, formation of coating layers having heat resistance is desirable. Furthermore, since the durability of the coating layers 64 and 69 of glass can be secured, the insulation property of the separator 60 can be maintained over a long period of time.

Furthermore, as shown, for example, in FIG. 2, a coating layer 35 may be formed on the inner circumferential surface of the sheath 30 as well. Preferably, the coating layer 35 is formed of fluorine, a fluorine compound, or glass. In the case where the coating layer 35 is formed on the inner circumferential surface of the sheath 30, even when a water droplet adhering to the surface of the separator 60 spreads because of surface tension thereof with resultant formation of a film of water, flow of leakage current between the connection terminals 44 and the sheath 30 can be prevented. Formation of the coating layer 35 on the inner circumferential surface of the sheath 30 is particular effective in the case where the coating layers 64 and 69 are formed of glass from the viewpoint of heat resistance as described above.

Moreover, coating layers may be formed on all components within the sheath 30 (not only on the inner circumferential surface of the sheath 30, but also on components accommodated within the sheath 30, such as the connection terminals 44, the separator 60, the metal holder 42, and the detection element 10). For example, the $NO_x$ sensor 1 is manufactured in a state in which a minute amount of a fluorine compound is placed in the sheath 30, and heat treatment or the like is performed such that the fluorine compound evaporates, whereby all the components within the sheath 30 are coated with the fluorine compound. In such a case, if coating is performed in a state in which the connection terminals 44 are in contact with the electrode pads 16 of the detection element 10, the contact points between the connection terminals 44 and the electrode pads 16 are not coated, and electrical connection therebetween is not hindered. Alternatively, in the case where the connection terminals 44 and the detection element 10 are coated in advance, coating is performed in a state in which portions serving as contact points are masked, and the masking is removed after formation of coating layers.

In the present embodiment, the separator 60 is a two-piece-type separator composed of the front separator 61 and the rear separator 66. However, the configuration of the separator is not limited thereto. The separator 60 may have a configuration in which the front separator and the rear separator are unitary molded. Alternatively, the separator 60 may have a configuration in which the separator is divided into two pieces along the axial direction of the detection element.

In the present embodiment, the $NO_x$ sensor 1, which can detect the concentration of $NO_x$, is described as an example of the gas sensor of the present invention. However, the gas sensor is not limited thereto. The present invention may be applied to various gas sensors, such as an oxygen sensor which detects the concentration of oxygen and which outputs a two-value signal (which changes sharply at a specific air-fuel ratio), a full-range air-fuel ratio sensor whose output changes linearly in accordance with the concentration of oxygen (linear oxygen sensor), and an HC sensor. In particular, the present invention is effective for a gas sensor configured such that a current equal to or less than 1 mA flows through a cell (a solid electrolyte member and a pair of detection electrodes) which constitutes a detection section of the detection element, and the concentration of a specific gas is detected on the basis of the current. The shape of the detection element is not limited to a plate-like shape, and the detection element may assume a tubular shape.

Example 1

The following evaluation test was carried out so as to check the effect of the invention attained through formation of a coating layer at least on the surface of the separator.

$NO_x$ sensors (Samples 1) were manufactured by use of separators coated with a fluorine compound, and 10 $NO_x$ sensors (Samples 2) were manufactured by use of separators without coating. In the course of manufacture of Samples 1 and Samples 2, the sheath and the metallic shell were joined together after one water droplet was dripped into the sheath, and the interior of the sheath was sealed. Samples 1 and Samples 2 were immersed into a bath (water bath) such that the entirety of each sample sank in water, and the bath was heated by a hot plate. In order to cause the water droplet to form dew, a cycle of heating each sample for 30 minutes (power ON) and then cooling each sample for 90 minutes (power off) was repeated ten times, and the water temperature was periodically changed between 40° C. and 100° C. After that test, water droplets adhering to the outer surface of each sample were wiped off, and the room-temperature insulation resistance of each sample was measured. The room-temperature insulation resistance refers to the insulation resistance, as measured at room temperature, between a lead wire having a connection terminal connected to an electrode pad corresponding to a heater electrode of the detection element and a lead wire having a connection terminal connected to another electrode pad corresponding to the $NO_x$ detection electrode (electrode of a cell whose output changes in accordance with $NO_x$ concentration) of the gas detection body. There was counted the number of samples whose insulation resistance was 20 MΩ or less and which failed to secure the insulation property of the separator when a voltage of 100 V was applied. None of the Samples 1 failed to secure the insulation property of the separator, and eight of the Samples 2 failed to secure the insulation property of the separator. Furthermore, a voltage of 100 V was applied between the sheath (sensor body earth) and the above-mentioned lead wire having a connection terminal connected to the electrode pad corresponding to the $NO_x$ detection electrode of the gas detection body, and the magnitude of leakage current flowing between the lead wire and the sheath was measured. At that time, there was counted the number of samples having a leakage current of 2 μA or more. None of Samples 1 had such leakage current, eight of Samples 2 had such leakage current. The results of this test reveal that, through application of fluorine coating on the separator, clearly, the insulation property of the separator can be secured, and leakage current within the sheath can be prevented.

DESCRIPTION OF REFERENCE NUMERALS

1: $NO_x$ sensor
10: detection element
12: rear end portion
16: electrode pad
30: sheath
44: connection terminal
50: metallic shell
60: separator
61: front separator
66: rear separator
64, 69: coating layer

The invention claimed is:

1. A gas sensor comprising:
   a detection element extending in an axial direction and adapted to detect the concentration of a specific gas;
   a metallic shell circumferentially surrounding and holding the detection element;
   a sheath attached to a rear end portion of the metallic shell and surrounding a rear end portion of the detection element; and
   a separator formed of an electrically insulating ceramic, disposed inside the sheath, and accommodating at least a plurality of conduction members for electrical connection with the detection element,
   the gas sensor being characterized in that a coating layer having water impermeability is directly formed on a surface of the separator.

2. The gas sensor according to claim 1, wherein the coating layer has water repellency.

3. The gas sensor according to claim 1, wherein the coating layer is formed of glass.

4. The gas sensor according to claim 1, wherein
   the detection element includes electrode pads formed on a rear end portion thereof for electrical connection with the conduction members;
   the separator further accommodates the rear end portion of the detection element; and
   the electrical connection between the conduction members and the electrode pads is established inside the separator.

5. The gas sensor according to claim 1, wherein the coating is formed of a fluorine compound.

* * * * *